United States Patent [19]

Goswami

[11] Patent Number: 5,175,100

[45] Date of Patent: Dec. 29, 1992

[54] STEREOSPECIFIC RESOLUTION BY HYDROLYSIS OF ESTERS OF 2-ARYLPROPIONIC ACIDS BY LIVER ENZYMES

[75] Inventor: Animesh Goswami, Princeton, N.J.

[73] Assignee: Rhone-Poulenc, Inc., Monmouth Junction, N.J.

[21] Appl. No.: 724,554

[22] Filed: Jun. 24, 1991

Related U.S. Application Data

[63] Continuation of Ser. No. 484,362, Feb. 26, 1990, abandoned.

[51] Int. Cl.$^5$ .............. C12P 7/40; C12P 7/64; C12N 9/18; C07P 41/00
[52] U.S. Cl. .................... 435/136; 435/134; 435/135; 435/141; 435/197; 435/280
[58] Field of Search ............... 435/134–136, 435/197, 280, 141

[56] References Cited

U.S. PATENT DOCUMENTS

| | | | |
|---|---|---|---|
| 4,650,755 | 3/1987 | Wood | 435/182 |
| 4,800,162 | 1/1989 | Matson | 435/136 |
| 4,857,462 | 8/1989 | Maier et al. | 435/197 |
| 4,886,750 | 12/1989 | Bertola et al. | 435/141 |

*Primary Examiner*—Herbert J. Lilling
*Attorney, Agent, or Firm*—Cushman, Darby & Cushman

[57] ABSTRACT

2-Arylpropionic acids such as ketoprofen, ibuprofen and naproxen can be stereospecifically resolved from their esters by hydrolysis using liver enzymes and particularly liver acetone powders derived from specific animals such as dog, pigeon, horse and goat.

16 Claims, No Drawings

STEREOSPECIFIC RESOLUTION BY HYDROLYSIS OF ESTERS OF 2-ARYLPROPIONIC ACIDS BY LIVER ENZYMES

This is a continuation of copending application Ser. No. 07/484,362 filed on Feb. 26, 1990 and now abandoned.

The present invention relates to the production of chiral 2-arylpropionic acids by using liver enzymes from various animal species.

A large number of 2-arylpropionic acids, e.g. ketoprofen, ibuprofen and naproxen, are used as nonsteroidal antiinflammatory agents. The 2-arylpropionic acids have two enantiomeric forms, i.e., the R- and S-enantiomers. It is well known that biological activity often is associated with only one enantiomer. For example, for the nonsteroidal antiinflammatory agents, such as ibuprofen, naproxen, and the like, activity lies with the S-enantiomer (J. Caldwell, A. J. Hutt, S. Fournel-Gigleux: *Biochemical Pharmacology*, 37, 105–114, 1988).

The 2-arylpropionic acids can be represented by the general structure of Formula I wherein Y is H:

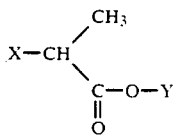

where X can be aromatic, substituted aromatic, heteroaromatic, and substituted heteroaromatic groups, each of which may be optionally substituted with other groups. If esters, Y represents an alcoholic residue.

Biochemical methods have been used for the isolation of chiral 2-arylpropionic acids as illustrated by the stereospecific hydrolysis of their esters (German Patent, DE No. 3345660, filed Dec. 16, 1983; European Patent No. 0227078, filed Dec. 19, 1986; European Patent No. 0233656, filed Jan. 6, 1987). These methods use either isolated enzymes or whole cells of microorganisms for the stereospecific hydrolysis. Enzymes from higher animals are not known to have been used for the stereospecific synthesis of these compounds.

The sterospecific hydrolysis of esters by enzymes from animal sources, especially from liver, have been mainly directed to the use of the esterase from porcine liver ("Enzymes in Organic Synthesis" J. B. Jones: *Tetrahedron*, 42, 3351–3403, 1986 and the references cited therein).

The enzymes from the livers of other species have been used only in a limited number of cases for sterospecific hydrolysis. For instance, enzymatic resolution of bicyclic lactones using horse liver esterase has been recently reported ("Enzymatic resolution of bicyclic lactones by horse liver esterases", E. Guibe et al., *Tetrahedron Letters*, 30, 67–68, 1989).

SUMMARY OF PRESENT INVENTION

In accordance with the invention, 2-arylpropionic acids can be stereo specifically resolved by hydrolysis from their esters using liver enzymes derived from certain animals sources enumerated hereinafter.

DETAILED DESCRIPTION OF THE INVENTION

As used herein the term "ketoprofen" is intended to mean "2-(3-benzoylphenyl)propionic acid"; ibuprofen" is intended to mean "2-(4-isobutylphenyl)propionic acid"; and naproxen is intended to mean "d-2-(6-methoxy-2-naphthyl) propionic acid".

The 2-arylpropionic acids which can be stereo specifically resolved by hydrolysis from their esters can be illustrated by the formula given as Formula I hereinbefore. Included within this group of compounds is ketoprofen, ibuprofen and naproxen. Thus X in the formula can be aryl, substituted aryl, heteroaryl, and substituted heteroaryl group. The aryl group may be any aryl group, such as, phenyl, naphthyl; the heteroaryl group may be any heteroaryl group, such as pyridyl, indolyl. The substitution on these aryl or heteroaryl group may be alkyl, aryl, heteroaryl, acyl, aroyl, heteroaroyl, alkoxy, aryloxy, heteroaryloxy, halogen, cyano, hydroxy, haloalkyl, haloaryl, hydroxyalkyl, hydroxyaryl groups. Y in the formula can be $C_1$–$C_{10}$ alkyl, including straight and branched chains and the halo (Cl, Br and I) and hydroxy substituted alkyl groups thereof, the condition being that the ester group is hydrolyzable by the enzyme. Preferably, the esters of 2-arylpropionic acid are the $C_1$ through $C_4$ alkyl esters of ketoprofen, ibuprofen and naproxen. Alkyl can be illustrated by methyl, ethyl, propyl, n-butyl; haloalkyl by 2-chloroethyl; and hydroxyalkyl by 2-hydroxyethyl, 2,3-dihydroxypropyl.

The 2-arylpropionic acids are optically active having one chiral center. Effective use of the acid as a pharmaceutical has dictated the resolution of the compound. The enzymes of the invention have the ability to resolve the acid into its dextro and levo-rotatory forms. The degree of resolution varies from enzyme to enzyme depending on the animal source. The effectiveness of an enzyme in resolution can be seen by the EE (enantiomeric excess) numbers.

The enzyme can be used in crude form, solvent treated or purified. Solvents which can be used to treat the enzyme include alcohols such as ethanol, hydrocarbons such as, hexane, isooctane and ketones such as acetone, preferably acetone. A purified enzyme can also be reproduced by cloning using state-of-the-art techniques. The use of liver acetone powders has been found to be effective in practicing the invention.

The liver acetone powders provide varying degree of activities. The stereospecificities of the hydrolysis depends on the source of liver acetone powder and on the substrate. Both the activity and stereospecificity could be increased by separating the constituents of liver acetone powder. In all cases, the unreacted ester contained preferential amount of the opposite enantiomer (opposite configuration of the acid preferentially produced in the hydrolysis by liver acetone powders). The unreacted ester could be converted by standard method, e.g. chemical hydrolysis, to provide an acid containing preferential amount of the opposite enantiomer to that produced by above hydrolysis by liver acetone powder. The liver acetone powders could also be used for the stereospecific synthesis of esters of 2-arylpropionic acids by driving the reaction in opposite direction by standard methodology, for example, by carrying out the ester synthesis in organic solvents. Alternatively, one ester with a certain alkyl or substituted alkyl group could be stereospecifically converted to other esters with different alkyl groups.

In its broadest aspects, the invention covers the use of liver enzymes of certain animal species to prepare acids from esters by hydrolysis using enzymes obtained from the livers of: rabbit, horse, sheep, pigeon, goat, seal, mouse, chicken, dog, rat, cat, calf, bovine, and mixtures thereof. Enzymes found to be substantially ineffective in hydrolyzing the 2-arylpropionic acid esters of the invention include those obtained from the livers of lemon shark, salmon, trout, turtle and guinea pig.

The criteria for the above grouping is based on the effectiveness of the enzymes in hydrolyzing the esters of the 2-arylpropionic as determined by the percentage of acid produced based on the weight of the original ester in an amount above 5% as listed in descending order of effectiveness. Bovine is included because of its effectiveness in resolution as indicated by its EE. Preferably, based on hydrolysis above 10% as above, the enzymes can be derived from the livers of rabbit, horse, sheep, pigeon, goat, seal and mixtures thereof and most preferably from the liver of rabbits and horses.

The enzymes which are effective in the invention as based on the ability to stereo specifically resolve the 2-arylpropionic acid, based on an entaniomeric excess (EE) of above 5% and in descending orders of effectiveness include the enzymes from the livers of dog, calf, bovine, pigeon, cat, horse, goat, rabbit, sheep, chicken, rat and mixtures thereof. Preferably, for EE's above 10%, enzymes from the livers of dog, calf, bovine, pigeon, cat, horse, goat and mixtures thereof.

Based on both percentage of acid above 10% and EE above 10%, the preferred overall enzymes are derived from the livers of dog, pigeon, horse, goat and mixtures thereof. While dog liver enzyme provided a percentage of acid produced at 8.0%, it is included in best overall because of EE of 74%.

The best overall enzyme is derived from the liver of dog.

These listings and numbers are based on the use of liver enzyme acetone powder. The use of crude or purified enzymes may change the order. This can be easily determined by an ordinary artisan using conventional tests. The general concept that crude enzymes are less effective than purified enzymes is applicable to the present invention.

The enzymes can be used free or immobilized by conventional means.

Suitable methods for immobilizing the enzymes for use herein are known in the art. See, for example, U.S. Pat. No. 4,436,813 which describes the immobilization of enzymes or cells containing the same using prepolymer materials such as polyaziridine prepolymers (i.e. Polycup), carboxymethyl cellulose, polymethylene isocyanate and polyurethane hydrogel prepolymers. Any of these materials may be used for present purposes in the manner described in U.S. Pat. No. 4,436,813. Also useful herein for immobilizing the enzyme are curable polyfunctional aziridine prepolymers as described in U.S. Pat. No. 4,650, 755 and Ser. No. 938,248, the contents of the patents and application mention in this paragraph being hereby incorporated by reference.

The enzymatic resolution can be carried out at any temperature range which is conducive to reaction and which does not inactivate the enzymes. High temperatures (i.e. >50° C.) are conducive to enzyme inactivation. Temperatures as low as 10° C. can be used though reaction rates are considerably lower. Effective temperatures vary somewhat depending on reactants and enzymes utilized. Advantageous results have been seen at temperatures ranging from about 25° C. to about 50° C., preferably from about 30° C. to about 40° C.

The pH utilized during the resolution reaction is that pH range conducive to efficient enzymatic reaction. While each enzyme has its own particular effective pH range, it has been found that pH's in general within the range of from about 5 to about 8.5 and preferably from about 6.5 to 7.5 are effective for the enzymes disclosed herein.

The reaction time used in the resolution is that time necessary to achieve the desired extent of reaction. Reaction times vary depending on the quantity, type and purity of the enzyme and the substrate and reaction times ranging from about ½ hour to several days are illustrative.

The incubation reaction can be conducted in aqueous solution or in mixed aqueous solution/organic solvent systems. The effectiveness of the mixed aqueous solution/organic solvent systems depend on the reactant, enzyme and organic solvent. The organic solvents can be derived from such sources as hydrocarbons, aromatic hydrocarbons, ethers, alcohols and other polar and nonpolar organic solvents. The solvents which can be used include from zero to 99% by volume water-miscible organic solvent. Water-immiscible solvents can be used with water to form a two phase solvent system, which can comprise from about zero to about 50% by volume aqueous component and corresponding from about 100% to about 50% water-immiscible organic solvent.

The water-miscible organic solvents can be illustrated by alcohols such as $C_1$–$C_3$ alcohols and 1 methoxy-2-propanol, glycols such as ethylene glycol propylene glycol, glycol ethers such as dimethyl ether of ethylene glycol, dimethyl ether of propylene glycol, dimethyl ether of diethylene glycol, dimethyl ether of tetraethylene glycol, and triols such as glycerol; cyclic oxides such as tetrahydrofuran and dioxane; ketones such as acetone and nitrogen containing compounds such as acetonitrile, dimethyl formamide, pyridine and mixtures thereof.

The water-immiscible organic solvents can be illustrated by hydrocarbons such as hexane, heptane, isooctane, decane, hexadecane, kerosene, petroleum ether, toluene and xylenes; chlorinated hydrocarbon such as methylene chloride and chloroform; esters such as ethyl acetate, ethers such as propyl ether, isopropyl ether, butyl ether, isobutyl ether, diethyl ether, methyl ethyl ether and diphenyl ether; and alcohols such as 2-ethyl-1-hexanol, 1-octanol, 2-octanol and mixtures thereof.

The resolved acids can be separated from the aqueous reaction solution by usual means including salting out, precipitation, extraction. The unresolved ester can be separated, racemized and recycled for further resolution.

The liver acetone powders used in the present invention were available from commercial sources and were bought from Sigma, USA. The esters of 2-arylpropionic acids were prepared in the conventional way and represented by the structure I where X represents the groups as described before and Y represents various alkyl and substituted alkyl groups. The hydrolysis reactions were performed in aqueous solutions with pHs ranging from 2 to 8 and at various temperatures ranging from 0° to 60° C. The esters were directly added to the reaction medium or dissolved in a small amount of organic solvent. The liver acetone powders as such or the hydrolytic enzymes of the liver acetone powders could be used for the process. Furthermore, the enzymes can be immobilized and reused.

The present invention is illustrated in the examples which follow.

EXAMPLE 1

A solution of 50 mg of ketoprofen methyl ester in 0.2 ml of ethanol was added to 10 mg of each of liver acetone powder from various animal sources (described in Table 1) in 5 ml of 0.1M potassium phosphate buffer (pH 7.0) After shaking at room temperature for 24 hours, the reaction mixtures were acidified to pH 2.0 with 6(N) HCl and extracted with 10 ml of ethyl acetate. A portion of the ethyl acetate extract was analyzed by HPLC on a Partisil 5 ODS-3 RAC column (9.4 mm×100 mm, Whatman) using a mixture of methanol and 10 mM ammonium dihydrogen phospate (9:1) and monitored by UV at 254 nm to determine the percentages of acid produced in the reaction. The results are summarized in Table I.

To determine the percentage of R- and S-acid, a portion of the ethyl acetate extract was converted to the amide derivative of the acid produced with R(+)-1-phenylethylamine as follows. The ethyl acetate extract (5 ml) was dried over sodium sulfate, filtered and cooled to 0° C. To the cold solution was added 0.2 ml of N-methylmorpholine followed by 0.2 ml of isobutyl chloroformate. After gentle shaking at 0° C. for 10 minutes, 0.2 ml of R(+)-1-phenylethylamine was added and the shaking was continued at 0° C. for 5 minutes and at room temperature for another 5 minutes. The reaction mixture was washed successively with water (5 ml), 1(N) HCl (5 ml), and water (5 ml) to provide the amide derivative in ethyl acetate solution. The ethyl acetate solution of the amide derivative was then analyzed by HPLC on the same column and same solvent mixture but with a different composition, i.e., a ratio of 6:4, and monitored by UV to determine the percentages of R-acid and S-acids produced by hydrolysis. The results are summarized in Table 1. The enantiomeric excess (EE) is defined as the difference in percent between the percent R- acid and the percent S-acid, the higher enantiomer being reported in the parenthesis in Table I.

TABLE 1

Hydrolysis of Methyl Ester of Ketoprofen by Liver Acetone Powders

| Liver acetone powder from | Percentage of acid | Percentage of Acid R-acid | S-acid | Percentage EE of acid (R or S) |
|---|---|---|---|---|
| Dog | 8.0 | 87.1 | 12.9 | 74.2 (R) |
| Calf | 5.7 | 71.6 | 28.4 | 43.2 (R) |
| Bovine | 4.3 | 71.2 | 28.8 | 42.4 (R) |
| Pigeon | 18.0 | 66.7 | 33.3 | 33.4 (R) |
| Cat | 7.2 | 64.1 | 35.9 | 28.2 (R) |
| Horse | 24.1 | 62.7 | 37.3 | 25.4 (R) |
| Goat | 15.5 | 42.3 | 57.7 | 15.4 (S) |
| Rabbit | 54.9 | 46.1 | 53.9 | 7.8 (S) |
| Sheep | 18.1 | 46.5 | 53.5 | 7.0 (S) |
| Chicken | 8.1 | 52.7 | 47.3 | 5.4 (R) |
| Rat | 7.5 | 52.7 | 47.3 | 5.4 (R) |
| Seal | 14.3 | 48.9 | 51.1 | 2.2 (S) |
| Mouse | 9.4 | 49.0 | 51.0 | 2.0 (R) |
| Lungfish | 3.2 | ND | ND | ND |
| Eel* | 3.0 | ND | ND | ND |
| Eel** | 1.1 | ND | ND | ND |
| Porcine | 0.9 | ND | ND | ND |
| Guinea Pig | 0.8 | ND | ND | ND |
| Trout | 0.7 | ND | ND | ND |
| Lemon Shark | 0.6 | ND | ND | ND |
| Salmon | 0.6 | ND | ND | ND |
| Turtle | 0.6 | ND | ND | ND |

*Anguilla anguilla
**Electrophorous electricus
ND—Not determined since percentage of acid was too low.

EXAMPLE 2

Several esters of ketoprofen (0.2 millimole) with various alkyl groups of varying chain length were hydrolyzed using liver acetone powders from bovine, calf and dog by the procedure described in Example 1. The reaction mixtures were analyzed by the same procedures as described in Example 1 and the results obtained are summarized in Table II.

TABLE II

Hydrolysis of Various Ketoprofen Esters by Liver Acetone Powders

| Liver Acetone Powder | Alkyl Chain of ester | Acid Produced (%) | Percent of Acid R-Acid | S-Acid | EE(%) of R-Acid |
|---|---|---|---|---|---|
| Bovine | C-1 | 4.4 | 73.6 | 26.4 | 47.2 |
|  | C-2 | 5.5 | 70.3 | 29.7 | 40.6 |
|  | C-3 | 3.4 | 70.7 | 29.3 | 41.4 |
|  | C-4 | 4.7 | 66.7 | 33.3 | 33.4 |
|  | C-6 | 3.3 | 72.7 | 27.3 | 45.4 |
|  | C-8 | 2.3 | 77.9 | 22.1 | 55.8 |
| Calf | C-1 | 7.3 | 72.8 | 27.2 | 45.6 |
|  | C-2 | 6.4 | 69.6 | 30.4 | 39.2 |
|  | C-3 | 5.0 | 69.1 | 30.9 | 38.2 |
|  | C-4 | 5.8 | 65.6 | 34.4 | 38.2 |
|  | C-6 | 5.4 | 71.0 | 29.0 | 42.0 |
|  | C-8 | 2.9 | 62.1 | 37.9 | 24.2 |
| Dog | C-1 | 6.2 | 88.3 | 11.7 | 76.6 |
|  | C-2 | 11.9 | 82.5 | 17.5 | 65.0 |
|  | C-3 | 6.1 | 84.1 | 15.9 | 68.2 |
|  | C-4 | 3.9 | 84.4 | 15.6 | 68.8 |
|  | C-6 | 3.9 | 67.9 | 32.1 | 35.8 |
|  | C-8 | 2.0 | 70.7 | 29.3 | 41.4 |

What is claimed is:

1. A process for sterospecifically hydrolyzing a racemic mixture of esters of 2-arylpropionic acid under such conditions as is necessary to stereospecifically hydroylze the ester, comprising contacting the said esters with an ester stereo specifically hydrolyzing liver enzyme derived from an animal selected from eh group consisting of dog, calf, bovine, pigeon, cat, horse, goat, rabbit, sheep, seal and mixtures thereof, and said enzyme being selected from the group consisting of a) ester sterospecifically hydrolyzing liver enzymes having a yield of at least 14.3% 2-arylpropionic acid and b) ester stereo specifically hydrolyzing liver enzymes having a yeild of 4.3–54.9% 2-arylpropionic acid and an enantiomeric excess (EE) of at least 15.4.

2. The process of claim 1 wherein the 2-arylpropionic acid resulting from the stereoselective hydrolysis is R-ketoprofen.

3. The process of claim 1 where the 2-arylpropionic acid resulting from the stereoselective hydrolysis is S-ketoprofen.

4. The process of claim 1 where the 2-arylpropionic acid resulting from the stereoselective hydrolysis is R-ibuprofen.

5. The process of claim 1 where the 2-arylpropionic acid resulting from the stereoselective hydrolysis is S-ibuprofen.

6. The process of claim 1 where the 2-arylpropionic acid resulting from the stereoselective hydrolysis is S-naproxen.

7. The process of claim 1 where the 2-arylpropionic acid resulting from the stereoselective hydrolysis is R-naproxen.

8. The process of claim 1 where the liver enzyme is derived from an animal selected from the group consisting of rabbit, horse, sheep, pigeon, goat, seal and mixtures thereof.

9. The process of claim 1 where the liver enzyme is derived from an animal selected from the group consisting of dog, pigeon, horse, goat and mixtures thereof.

10. The process of claim 6 where the liver enzyme is derived from an animal selected from the group consisting of dog, calf, bovine, pigeon, cat, horse, goat and mixtures thereof.

11. The process of claim 1 where the liver enzyme is derived from the liver of dog.

12. The process as recited in claim 1 where the liver enzyme is selected from the group consisting of crude enzyme, solvent treated liver enzyme and purified liver enzyme.

13. The process of claim 11 wherein the liver enzyme is a solvent treated liver enzyme and the solvent is acetone.

14. The process as recited in claim 1 wherein the liver enzyme is immobilized.

15. The process as recited in claim 14 wherein the liver enzyme is immobilized by absorbing the enzyme on an ion exchange resin followed by contacting the so absorbed enzyme with a polyaziridine prepolymer.

16. The process of claim 1 wherein said stereo specifically hydrilyzed esters of 2-arylpropionic acid result in stereoisomers of 2-arylpropionic acid present in enantiomeric excess ranging from 5.4–74.2%.

* * * * *